United States Patent
Mueller et al.

(10) Patent No.: US 6,406,181 B1
(45) Date of Patent: Jun. 18, 2002

(54) TEMPERATURE SENSOR

(75) Inventors: Bernd Mueller, Leonberg; Thomas Brinz, Bissingen Unter Der Teck; Bernd Schumann, Rutesheim, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/522,539

(22) Filed: Mar. 10, 2000

(30) Foreign Application Priority Data

Mar. 10, 1999 (DE) .......................................... 199 10 444

(51) Int. Cl.[7] .............................. G01K 7/26; G01N 25/00
(52) U.S. Cl. ...................... 374/185; 338/2.5; 73/25.01; 73/25.03; 73/25.05
(58) Field of Search ................................. 374/183, 185; 73/25.01, 25.03, 25.05; 204/431; 338/25, 35, 34, 23

(56) References Cited

U.S. PATENT DOCUMENTS

| | | | |
|---|---|---|---|
| 4,169,778 A | * 10/1979 | Mann et al. | 204/195 S |
| 4,309,688 A | * 1/1982 | Kempe | 338/25 |
| 4,880,519 A | * 11/1989 | Wang et al. | 204/425 |
| 4,951,028 A | * 8/1990 | Tuller | 338/22 R |
| 5,172,466 A | * 12/1992 | Friese et al. | 29/612 |
| 5,199,791 A | * 4/1993 | Kasanami et al. | 374/185 |
| 5,430,428 A | * 7/1995 | Gerblinger et al. | 338/25 |
| 5,795,545 A | * 8/1998 | Koripella et al. | 422/94 |
| 5,823,680 A | * 10/1998 | Kato et al. | 374/185 |
| 6,136,170 A | * 10/2000 | Inoue et al. | 204/424 |
| 6,175,749 B1 | * 1/2001 | Wordenweber | 505/191 |
| 6,337,006 B1 | * 1/2002 | Fujita et al. | 204/421 |

FOREIGN PATENT DOCUMENTS

| | | |
|---|---|---|
| DE | 27 50 049 | 5/1979 |
| DE | 38 06 308 | 9/1989 |
| DE | 40 20 383 | 1/1992 |
| DE | 40 20 385 | 1/1992 |
| EP | 0853239 A2 * | 1/2001 |
| JO | 2087032 * | 3/1990 |
| JO | 3010131 * | 1/1991 |
| JP | 04064051 * | 2/1992 |
| JP | 05296975 A * | 11/1993 |
| JP | 06308076 * | 11/1994 |
| JP | 10282031 A * | 10/1998 |

* cited by examiner

*Primary Examiner*—Diego Gutierrez
*Assistant Examiner*—Gail Verbitsky
(74) *Attorney, Agent, or Firm*—Kenyon & Kenyon

(57) ABSTRACT

A temperature sensor, in particular for a gas sensor, has at least one printed conductor, where a temperature-dependent change in a resistance of the printed conductor is detected and analyzed. The printed conductor has at least one section made of a solid electrolyte.

6 Claims, 1 Drawing Sheet

TEMPERATURE SENSOR

FIELD OF THE INVENTION

The present invention relates to a temperature sensor, in particular for a gas sensor.

BACKGROUND INFORMATION

Temperature sensors are known. They are used in gas sensors to detect and regulate an operating temperature of the gas sensor. Such gas sensors are needed, for example, to determine the oxygen partial pressure in the exhaust gas from an internal combustion engine. They are usually constructed in layers, with the individual layers containing the elements needed to ensure functionality.

The individual layers are made of a ceramic material which is permanently applied by film casting, punching, screen printing, laminating, cutting, sintering or the like. Individual ceramic layers have a printed conductor made of a cermet or they are made of a solid electrolyte and thus have the ability to conduct electricity. Such gas sensors have at least one area where a solid electrolyte is applied between at least two cermet electrodes. The conductivity of the solid electrolyte varies as a function of the oxygen partial pressure, for example, and thus is a direct measure of the oxygen concentration in the exhaust gas. However, for an exact determination of the measured value, the temperature must be above 300° C. because the solid electrolyte has the required basic conductivity only above such a temperature, and gas sensors therefore have at least one heating device.

On the other hand, the temperature of the exhaust gas varies greatly during operation of an internal combustion engine. Since the conductivity of the solid electrolyte depends on temperature, this change in temperature must be determined.

It is known that such gas sensors may be equipped with temperature sensors to detect and analyze a temperature-dependent change in resistance of a printed conductor.

First, the resistance of the printed conductor of the heating device may be measured. Printed conductors are usually made of a cermet, using platinum, for example, as the metal. The resistance is then dominated by the metallic conducting platinum. One disadvantage of this is that the resistance temperature coefficient is low, and this low dependence of resistance on temperature is often inadequate to construct a suitable control device.

In addition, temperature can be detected on the basis of the resistance of the solid electrolyte, in which case the solid electrolyte with the known sensors has a double function. The solid electrolyte has a much higher resistance temperature coefficient. A disadvantage of the known methods is that the resistance also depends on various external factors such as the oxygen partial pressure, activation, aging and poisoning, so that accurate determination of the measured value is no longer possible.

SUMMARY OF THE INVENTION

The temperature sensor according to the present invention offers the advantage that it permits much more accurate determination of measured values. Due to the fact that the printed conductor has at least one section made of a solid electrolyte, the favorable resistance temperature coefficient can be utilized while, on the other hand, this section is not exposed to the various interfering external factors such as poisoning, activation, aging and oxygen partial pressure.

It is especially advantageous to cover the printed conductor of the temperature sensor with an insulation layer. Such an insulation layer may be made of aluminum oxide, for example.

It is also advantageous to integrate the temperature sensor into a layer carrying the heating device, because it is delineated from the other elements of the gas sensor by insulation layers. In this case, to simplify the production of the gas sensor, a partial section of the printed conductor of the heating device may correspond to a partial section of the printed conductor of the temperature sensor. The section of the temperature sensor having the solid electrolyte is in contact with the printed conductor of the heating device and is also in contact with a printed conductor of the temperature sensor.

It is also preferable for the temperature-dependent change in resistance to be detected by an alternating voltage acting on it.

DETAILED DESCRIPTION

Figure 1:
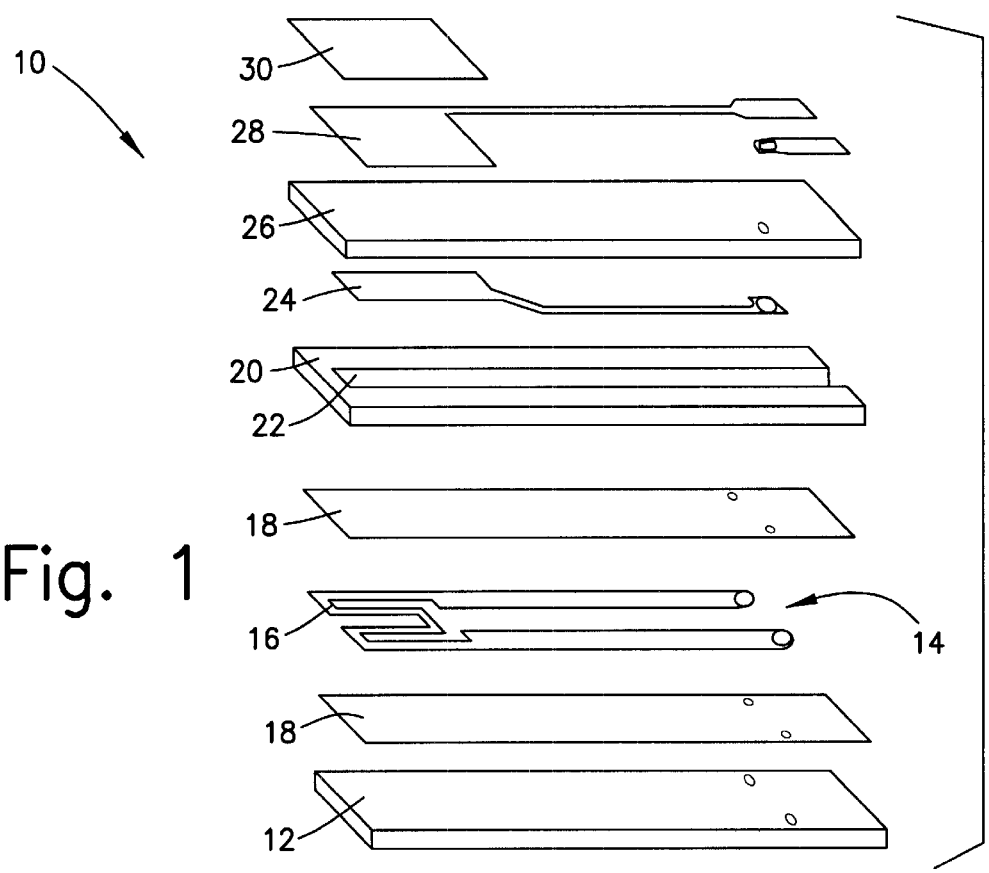
FIG. 1 shows a schematic exploded view of a gas sensor.

FIG. 1 shows a schematic exploded view of the structure of a gas sensor 10. The individual layers are formed by film casting, punching, screen printing, laminating, cutting, sintering or the like. Gas sensor 10 illustrated here by way of an example is composed of a carrier layer 12 to which a heating device 14 is applied. Heating device 14 usually has a printed conductor 16 made of a cermet, for example, and shielded by two insulation layers 18.

In addition, such a gas sensor 10 has a layer 20 with a recess 22 in which a reference gas is enclosed. Above recess 22 there is a cermet electrode 24 which is covered by a layer of a solid electrolyte 26. A second cermet electrode 28 follows and is covered by a porous protective layer 30.

The functioning of a gas sensor 10 is known and will not be explained further within the scope of this description. The necessary prerequisite for operation is to first reach a temperature of more than 300° C. which is made possible by heating device 14, and it is also necessary to detect an actual temperature for determination of a temperature-dependent correction factor for determination of the measured value.

Figure 2:
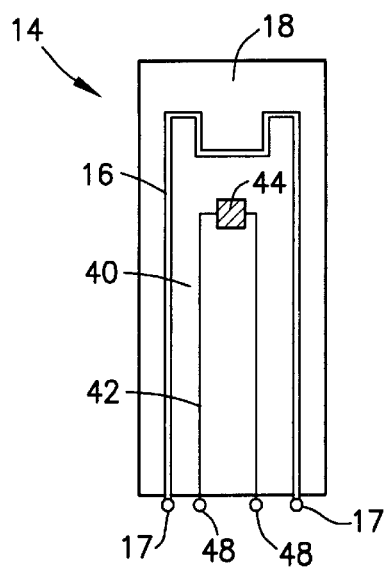
FIG. 2 shows a schematic top view of an embodiment of a temperature sensor.

FIG. 2 shows a top view of a temperature sensor 40 according to the present invention accommodated in the area of heating device 14. Of course, temperature sensor 40 may also be arranged in other areas of gas sensor 10. However, it is especially advantageous due to manufacturing considerations to arrange it in the area of heating device 14 because the necessary insulation layers 18 are present there.

Temperature sensor 40 has a printed conductor 42 having at least one section 44 of a solid electrolyte. Printed conductor 42 of temperature sensor 40, like printed conductor 16 of heating device 14, is arranged between two insulation layers 18 and is thus protected from interfering external influences. By applying an alternating voltage to the contact points 48, a conductivity is measured. Because of the great resistance temperature coefficient of printed conductor 42 in section 44, a sufficient dependence of the resistance on temperature is achieved for suitable temperature control. The components of gas sensor 10 needed for analysis and control of the temperature are not shown for reasons of simplicity.

Figure 3:
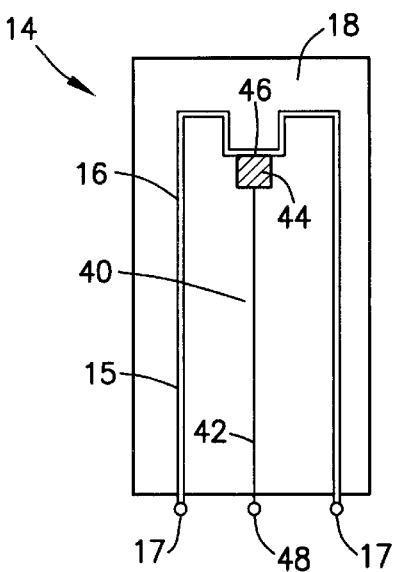
FIG. 3 shows a schematic top view of an alternative embodiment of a temperature sensor.

FIG. 3 shows an alternative embodiment of temperature sensor 40. A partial section 15 of printed conductor 16 of heating device 14 is also at the same time a partial section 15 of printed conductor 42 of temperature sensor 40. In this way, the number of contact points is smaller and the material costs are also reduced. During the measurement, printed conductor 42 receives an alternating voltage at contact points 17, 48. The alternating voltage may have superimposed on it a d.c. voltage which is necessary for operation of heating device 14, or the voltage for heating operation is interrupted during the measurement.

Stabilized zirconium dioxide, for example, may be used as the solid electrolyte for section 44 because it can be incorporated especially easily by conventional production methods. As an alternative, however, other materials having marked changes in resistance in the temperature range of operation would also be suitable.

What is claimed is:

1. A temperature sensor for a gas sensor, comprising:
    at least one printed conductor having at least one section made of a solid electrolyte; and
    means for detecting and analyzing a temperature-dependent change in a resistance of the at least one printed conductor.

2. The temperature sensor according to claim 1, further comprising two insulation layers, the at least one printed conductor being situated between the two insulation layers.

3. The temperature sensor according to claim 2, further comprising a heating device, the at least one printed conductor being situated in a layer carrying the heating device covered by the two insulation layers.

4. The temperature sensor according to claim 3, wherein the heating device includes a further printed conductor, a partial section of the further printed conductor of the heating device corresponding to a partial section of the at least one printed conductor.

5. The temperature sensor according to claim 1, further comprising means for applying an alternating voltage to the at least one printed conductor to detect a resistance of the at least one printed conductor.

6. The temperature sensor according to claim 1, wherein the solid electrolyte includes zirconium dioxide.

* * * * *